United States Patent
Loria

(10) Patent No.: US 9,662,241 B1
(45) Date of Patent: May 30, 2017

(54) PENILE TENSION SYSTEM

(71) Applicant: Victor Loria, Doral, FL (US)

(72) Inventor: Victor Loria, Doral, FL (US)

( * ) Notice: Subject to any disclaimer, the term of this patent is extended or adjusted under 35 U.S.C. 154(b) by 210 days.

(21) Appl. No.: 14/696,970

(22) Filed: Apr. 27, 2015

(51) Int. Cl.
*A61F 5/41* (2006.01)
*A61F 5/01* (2006.01)
*A61B 19/00* (2006.01)

(52) U.S. Cl.
CPC ............ *A61F 5/0104* (2013.01); *A61B 19/24* (2013.01)

(58) Field of Classification Search
CPC .. A61F 5/41; A61H 19/30; A61H 1/02; A61H 2001/0203; A61H 1/0218; A61H 2205/087
USPC ...................................................... 600/38–41
See application file for complete search history.

(56) References Cited

U.S. PATENT DOCUMENTS

| 4,844,103 A * | 7/1989 | Vick ......................... A45D 2/18 132/245 |
| 2016/0235580 A1* | 8/2016 | Trost ......................... A61F 5/41 |

* cited by examiner

*Primary Examiner* — John Lacyk

(57) ABSTRACT

A penile tension system features a semi-hard, semi-flexible cylindrical rod having a first handle and a second handle. The system features a soft, flexible noose member located on a cylindrical rod side wall. The system features an elastomeric linear fastening member. The system features a series of markings located on the rod side wall.

4 Claims, 3 Drawing Sheets

PENILE TENSION SYSTEM

FIELD OF THE INVENTION

The present invention relates to tension systems for use with humans, or more specifically, tension systems and methods for use with a human penis.

BACKGROUND OF THE INVENTION

In some cases, individuals may wish to apply tension to a penis in an attempt to change a size or shape of the penis. The present invention features a penile tension system.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a penile tension system. In some embodiments, the system comprises a semi-hard, semi-flexible cylindrical rod. In some embodiments, the system comprises a first handle and a second handle. In some embodiments, the system comprises a soft, flexible noose member located on a cylindrical rod side wall. In some embodiments, the system comprises an elastomeric linear fastening member. In some embodiments, the system comprises a series of markings located on the rod side wall.

In some embodiments, a distal end of a penis (a glans) is inserted into the noose member for a temporary gripping attachment. In some embodiments, the penis is rolled around the cylindrical rod via rotation of the first handle and the second handle. In some embodiments, tension is applied to the rolled penis. In some embodiments, the fastening member is attached over the rolled penis via attaching a first fastening aperture to the first handle and a second fastening aperture to the second handle.

DESCRIPTION OF PREFERRED EMBODIMENTS

Figure 1:
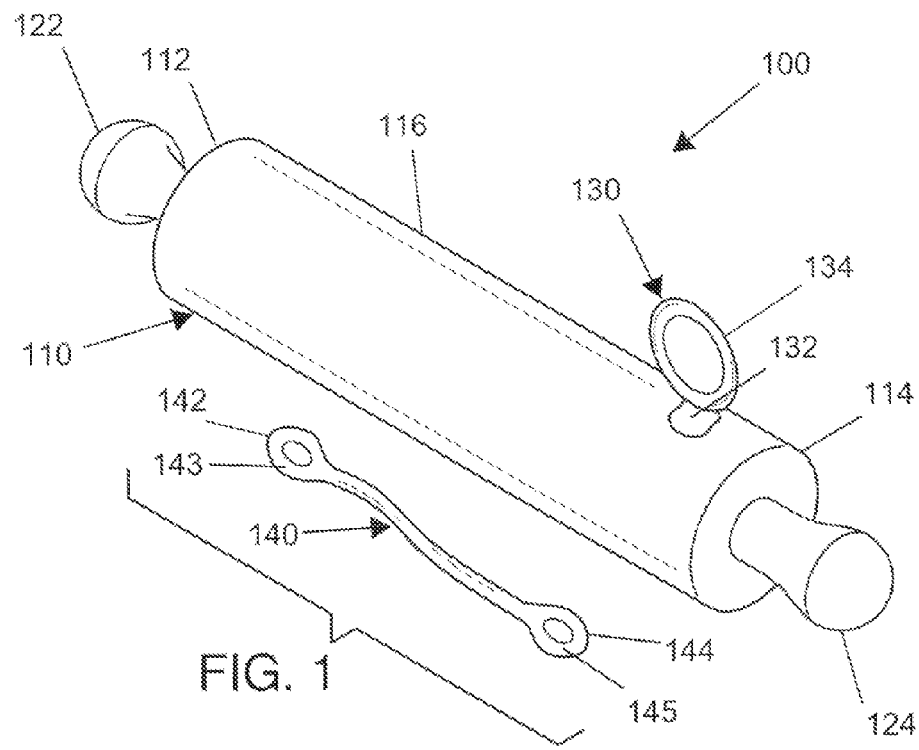
FIG. 1 shows a perspective view of the present invention.
Figure 2:
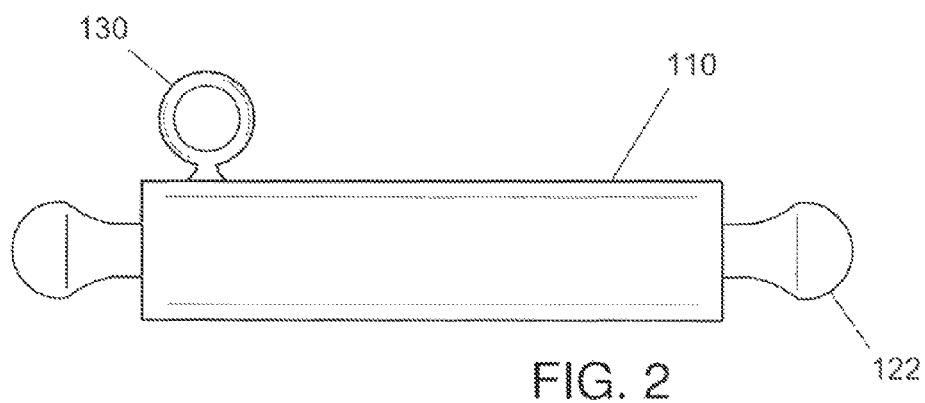
FIG. 2 shows a front view of the cylindrical rod and the noose member of the present invention.
Figure 3:
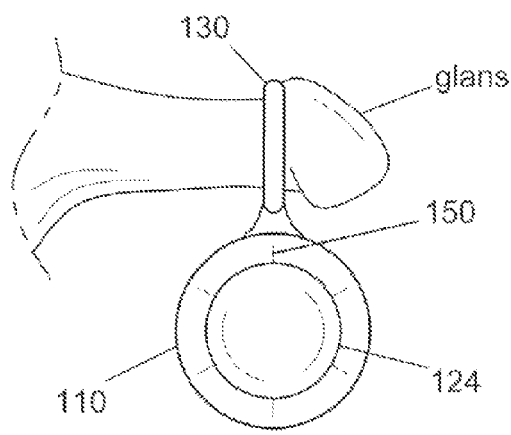
FIG. 3 shows a side view of the cylindrical rod and the noose member of the present invention in use in a first position.
Figure 4:
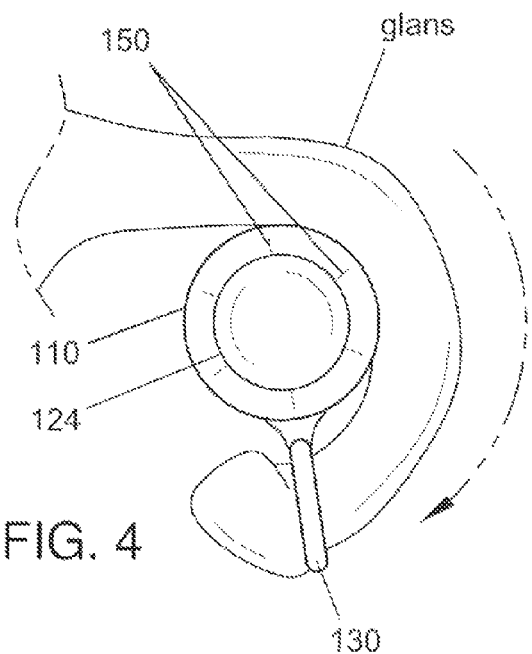
FIG. 4 shows a side view of the cylindrical rod and the noose member of the present invention in use in a second position.
Figure 5:
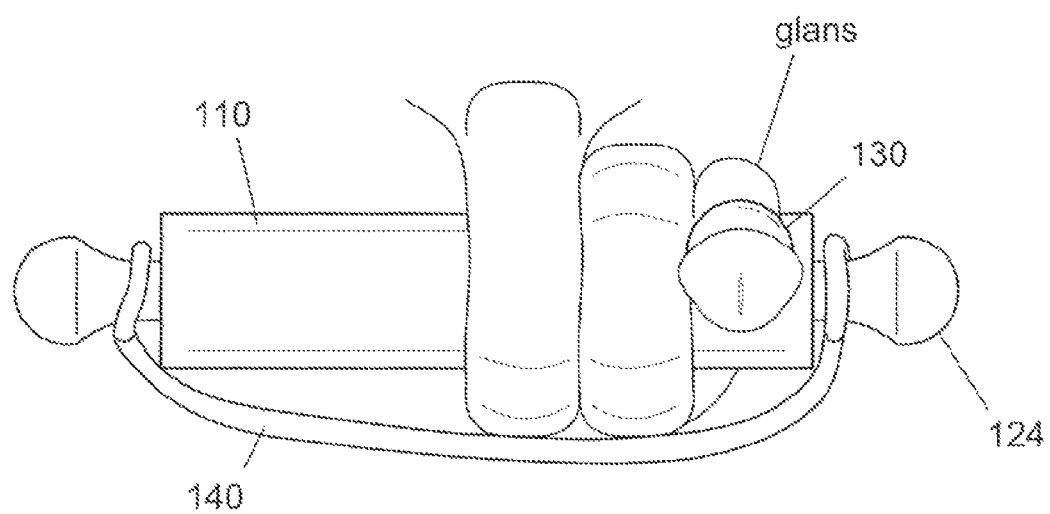
FIG. 5 shows a front view of the present invention in use in a third position.

Following is a list of elements corresponding to a particular element referred to herein:
100 Penile tension system
110 Cylindrical rod
112 Rod first end
114 Rod second end
116 Rod side wall
122 First handle
124 Second handle
130 Noose member
132 Offset member
134 Ring
140 Fastening member
142 Fastening member first end
143 First fastening aperture
144 Fastening member second end
145 Second fastening aperture
150 Marking Referring now to FIG. 1-5, the present invention features a penile tension system (100). In some embodiments, the system (100) comprises a semi-hard, semi-flexible, linear cylindrical rod (110) having a rod first end (112), a rod second end (114), and a rod side wall (116).

In some embodiments, the system (100) comprises a first handle (122) affixedly located on and projecting out and away from the rod first end (112) and a second handle (124) affixedly located on and projecting out and away from a rod second end (114).

In some embodiments, the system (100) comprises a soft, flexible noose member (120) located on and projecting out and away from the cylindrical rod side wall (116). In some embodiments, the system (100) comprises a semi-hard, semi-flexible noose member (120) located on and projecting out and away from the cylindrical rod side wall (116). In some embodiments, the noose member (120) comprises a linear offset member (132) having a ring (134) located on an offset member end thereon.

In some embodiments, the system (100) comprises an elastomeric linear fastening member (140) having a fastening member first end (142) and a fastening member second end (144). In some embodiments, a first fastening aperture (143) is located on the fastening member first end (142) and a second fastening aperture (145) is located on the fastening member second end (144).

In some embodiments, the system (100) comprises a series of markings (150) located on the rod side wall (116).

In some embodiments, a distal end of a penis (a glans) is inserted into the noose member (120) for a temporary gripping attachment. The noose member (120) is adapted to safely and painlessly grip the distal end of the penis. In some embodiments, the penis is rolled around the cylindrical rod (110) via rotation of the first handle (122) and the second handle (124). In some embodiments, tension is applied to the rolled penis and held. In some embodiments, the fastening member (140) is attached over the rolled penis via attaching the first fastening aperture (143) to the first handle (122) and the second fastening aperture (145) to the second handle (124). In some embodiments, the fastening member (140) secures the penis in place via tension on the rolled side. In some embodiments, a change in penis size or shape of the penis can be determined via a position of a base of the penis relative to the series of markings (150).

In some embodiments, the semi-hard cylindrical rod (110) comprises silicone.

In some embodiments, the noose member (120) comprises silicone. In some embodiments, the noose member (120) stretches around the distal end of the penis. In some embodiments, the noose member (120) grips the distal end of the penis.

In some embodiments, the present invention features a method of applying tension to a penis. In some embodiments, the method comprises obtaining a penile tension system (100).

In some embodiments, the method comprises inserting a distal end of a penis (a glans) into a noose member (120) for a temporary gripping attachment.

In some embodiments, the method comprises rolling the penis around a cylindrical rod (110) via rotation of a first handle (122) and a second handle (124).

In some embodiments, the method comprises applying tension to the rolled penis via rolling.

In some embodiments, the method comprises attaching a fastening member (140) over the rolled penis to hold tension thereon via attaching a first fastening aperture (143) to a first handle (122) and a second fastening aperture (145) to a second handle (124).

In some embodiments, the method comprises determining a shape or size change of the penis via measuring a position of a base of the penis relative to a series of markings.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A penile tension system (100), wherein the system (100) comprises:
    (a) a semi-hard, semi-flexible, linear cylindrical rod (110) having a rod first end (112), a rod second end (114), and a rod side wall (116);
    (b) a first handle (122) affixedly disposed on and projecting out and away from the rod first end (112) and a second handle (124) affixedly disposed on and projecting out and away from a rod second end (114);
    (c) a soft, flexible noose member (120) disposed on and projecting out and away from the cylindrical rod side wall (116), wherein the noose member (120) comprises a linear offset member (132) having a ring (134) disposed on an offset member end thereon;
    (d) an elastomeric linear fastening member (140) having a fastening member first end (142) and a fastening member second end (144), wherein a first fastening aperture (143) is disposed on the fastening member first end (142) and a second fastening aperture (145) is disposed on the fastening member second end (144);
    (e) a series of markings (150) disposed on the rod side wall (116);

wherein a distal end of a penis (a glans) is inserted into the noose member (120) for a temporary gripping attachment, wherein the penis is rolled around the cylindrical rod (110) via rotation of the first handle (122) and the second handle (124), wherein tension is applied to the rolled penis, wherein the fastening member (140) is attached over the rolled penis via attaching the first fastening aperture (143) to the first handle (122) and the second fastening aperture (145) to the second handle (124), wherein a change in penis size or shape of the penis can be determined via a position of a base of the penis relative to the series of markings (150).

2. The system (100) of claim 1, wherein the semi-hard cylindrical rod (110) comprises silicone.

3. The system (100) of claim 1, wherein the noose member (120) comprises silicone.

4. A method of applying tension to a penis, wherein the method comprises:
    (a) obtaining a penile tension system (100);
    (b) inserting a distal end of a penis (a glans) into a noose member (120) for a temporary gripping attachment;
    (c) rolling the penis around a cylindrical rod (110) via rotation of a first handle (122) and a second handle (124);
    (d) applying tension to the rolled penis via rolling;
    (e) attaching a fastening member (140) over the rolled penis to hold tension thereon via attaching a first fastening aperture (143) to a first handle (122) and a second fastening aperture (145) to a second handle (124); and
    (f) determining a shape or size change of the penis via measuring a position of a base of the penis relative to a series of markings.

* * * * *